United States Patent
Kohler

(10) Patent No.: US 10,694,932 B2
(45) Date of Patent: *Jun. 30, 2020

(54) DENTAL INSTRUMENT CAMERA APPARATUS

(71) Applicant: ONVI, Inc., Wilmette, IL (US)

(72) Inventor: Craig S. Kohler, Glenview, IL (US)

(73) Assignee: ONVI, Inc., Wilmette, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,248

(22) Filed: Jul. 18, 2017

(65) Prior Publication Data
US 2018/0070807 A1    Mar. 15, 2018

Related U.S. Application Data

(63) Continuation of application No. 14/645,145, filed on Mar. 11, 2015.

(Continued)

(51) Int. Cl.
| | |
|---|---|
| A61B 1/24 | (2006.01) |
| A61B 1/247 | (2006.01) |
| A61C 15/02 | (2006.01) |
| A61C 17/22 | (2006.01) |
| A46B 15/00 | (2006.01) |
| A61C 15/04 | (2006.01) |
| A61C 17/20 | (2006.01) |
| A61B 1/00 | (2006.01) |
| A61C 1/08 | (2006.01) |

(52) U.S. Cl.
CPC .......... *A61B 1/247* (2013.01); *A46B 15/0036* (2013.01); *A61B 1/00016* (2013.01); *A61B 1/00087* (2013.01); *A61C 15/02* (2013.01); *A61C 15/046* (2013.01); *A61C 17/20* (2013.01); *A61C 17/22* (2013.01); *A61C 1/088* (2013.01)

(58) Field of Classification Search
CPC ...................................................... A61B 1/247
See application file for complete search history.

(56) References Cited

U.S. PATENT DOCUMENTS

| | | |
|---|---|---|
| 4,137,926 A | 2/1979 | Pao |
| 4,915,626 A | 4/1990 | Lemmey |

(Continued)

FOREIGN PATENT DOCUMENTS

| | | |
|---|---|---|
| CN | 102245123 A | 11/2011 |
| EP | 1033942 B1 | 9/2009 |

(Continued)

OTHER PUBLICATIONS

The State Intellectual Property Office of China, Office Action on Appl. No. 201580023769.8, dated Sep. 28, 2017, 10 pgs.

(Continued)

*Primary Examiner* — Eric D. Bertram
(74) *Attorney, Agent, or Firm* — Greenberg Traurig, LLP

(57) ABSTRACT

The present invention relates to dental instruments having video capabilities. Specifically, the present invention relates to a dental instrument having a video camera for viewing a user's or patient's mouth when utilizing the dental instrument. More specifically, the dental instrument provides video output to a wireless device, such as a smart phone, tablet computer or other like computer. Methods of using the same are further provided.

12 Claims, 5 Drawing Sheets

Related U.S. Application Data

(60) Provisional application No. 61/951,437, filed on Mar. 11, 2014.

(56) References Cited

U.S. PATENT DOCUMENTS

| | | | |
|---|---|---|---|
| 5,016,098 A | | 5/1991 | Cooper et al. |
| 5,027,138 A | * | 6/1991 | Gandrud ............... A61B 1/042 |
| | | | 348/66 |
| 5,049,070 A | | 9/1991 | Ademovic |
| 5,051,823 A | | 9/1991 | Cooper et al. |
| 5,052,924 A | | 10/1991 | Berg |
| 5,115,307 A | | 5/1992 | Cooper et al. |
| 5,178,536 A | | 1/1993 | Werly et al. |
| 5,230,621 A | | 7/1993 | Jacoby |
| 5,251,025 A | | 10/1993 | Cooper |
| 5,290,168 A | | 3/1994 | Cooper et al. |
| 5,484,283 A | | 1/1996 | Franetzki |
| 5,527,261 A | | 6/1996 | Monroe et al. |
| 5,634,790 A | | 6/1997 | Pathmanabhan et al. |
| 5,743,731 A | * | 4/1998 | Lares ............... A61B 1/00087 |
| | | | 433/29 |
| 6,007,333 A | | 12/1999 | Callan et al. |
| 6,102,695 A | | 8/2000 | Rosenstatter |
| 6,468,076 B2 | | 10/2002 | Kawamura |
| 6,511,323 B1 | | 1/2003 | Wilkinson |
| 6,658,471 B1 | | 12/2003 | Berry et al. |
| 6,685,471 B1 | * | 2/2004 | Kawamura ........ A46B 15/0002 |
| | | | 15/105 |
| 6,895,624 B2 | * | 5/2005 | Fischer ................ A61B 17/244 |
| | | | 132/308 |
| 7,104,792 B2 | | 9/2006 | Taub et al. |
| 7,713,058 B2 | | 5/2010 | Takahashi |
| 7,806,690 B2 | | 10/2010 | Heath et al. |
| 8,839,476 B2 | | 9/2014 | Adachi |
| 8,938,838 B2 | | 1/2015 | Vashi |
| 9,247,882 B2 | | 2/2016 | Hakomori et al. |
| 2004/0076019 A1 | * | 4/2004 | Tsimerman ........ A61B 1/00096 |
| | | | 362/580 |
| 2006/0166162 A1 | | 7/2006 | Ting |
| 2008/0096154 A1 | | 4/2008 | Rakocz |
| 2009/0176185 A1 | | 7/2009 | Chen |
| 2011/0315572 A1 | | 12/2011 | Vu et al. |
| 2012/0040305 A1 | * | 2/2012 | Karazivan .......... A61B 1/00087 |
| | | | 433/29 |
| 2015/0037751 A1 | | 2/2015 | Motoyama |
| 2016/0038033 A1 | | 2/2016 | Lal |

FOREIGN PATENT DOCUMENTS

| | | |
|---|---|---|
| EP | 2712178 | 3/2014 |
| EP | 2891467 A1 | 7/2015 |

OTHER PUBLICATIONS

International Search Report, dated Aug. 20, 2015, and Written Opinion, completed Jul. 21, 2015, for the counterpart patent application PCT/US2015/019996, 6 pgs.

\* cited by examiner

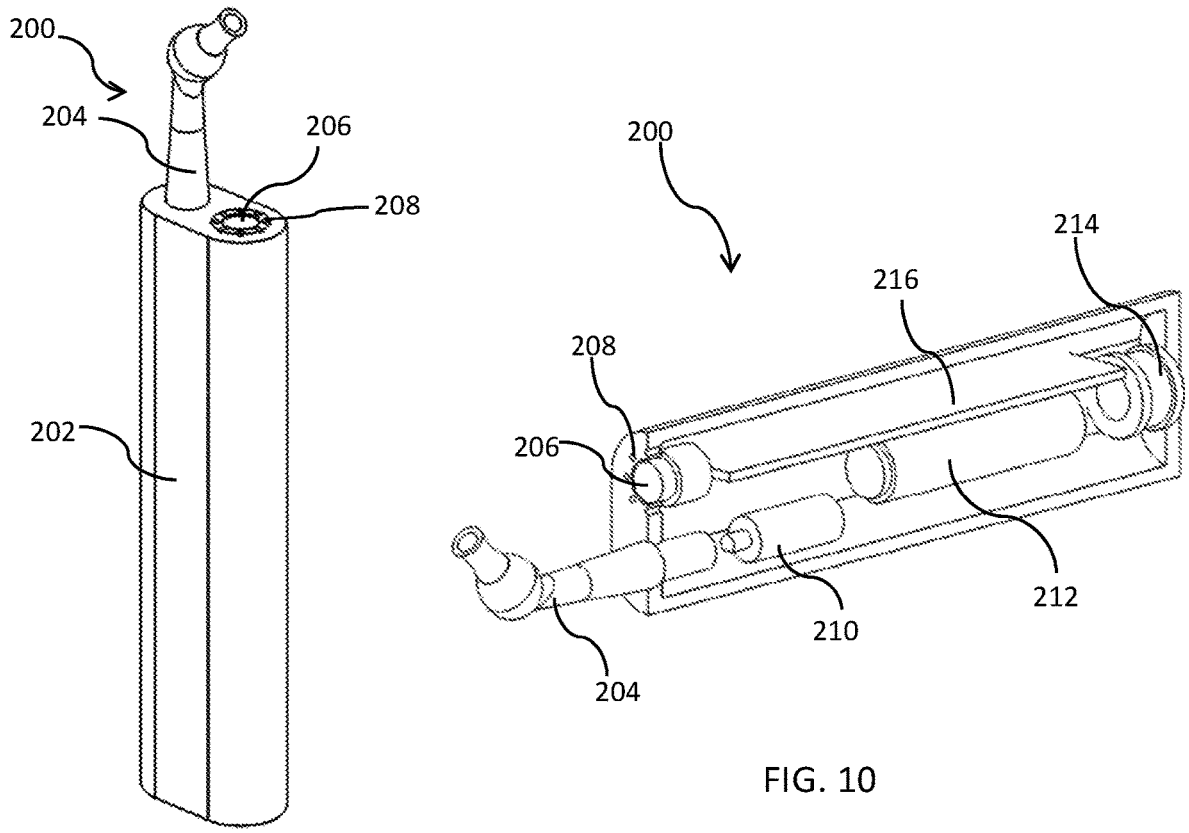
FIG. 9
FIG. 10
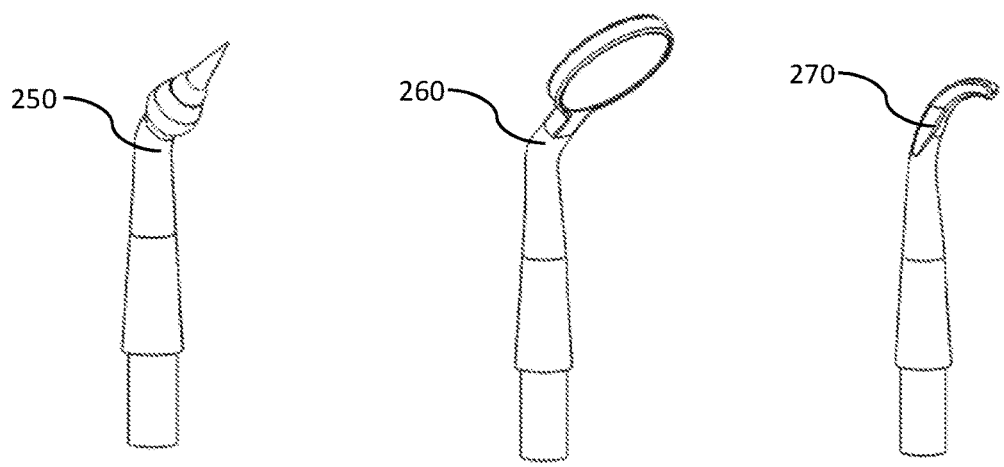
FIG. 11A
FIG. 11B
FIG. 11C

DENTAL INSTRUMENT CAMERA APPARATUS

This application is a continuation of U.S. application Ser. No. 14/645,145 and claims priority under 35 U.S.C. 119 to U.S. Provisional Patent App. No. 61/951,437, "Dental Instrument Camera Apparatus and Methods of Using the Same," filed Mar. 11, 2014, which is incorporated herein by reference in its entirety.

TECHNICAL FIELD

The present invention relates to dental instruments having video capabilities. Specifically, the present invention relates to a dental instrument having a video camera for viewing a user's or patient's mouth when utilizing the dental instrument. More specifically, the dental instrument provides video output to a wireless device, such as a smart phone, tablet computer or other like computer. Methods of using the same are further provided.

BACKGROUND

Individuals have used dental instruments for centuries to care for teeth. Specifically, individuals primarily use toothbrushes and dental floss for brushing plaque from teeth and removing food debris from between teeth that otherwise may cause tooth decay and cavities. Indeed, humans have used some form of tooth care since the dawn of recorded history in the form of twigs or tooth picks. Bristly toothbrushes have been traced back to the Tang dynasty in early Chinese history.

Dentists are health practitioners that specialize in the diagnosis, prevention, and treatment of diseases and conditions of the oral cavity. Specifically, dentists primarily take care of patients' teeth using a variety of instruments, including, for example, brushes, scalers, curettes, drills and other like instruments for cleaning and repairing teeth. In use, these instruments are typically placed inside the oral cavity of a patient and manipulated for their purpose to clean, restore and/or repair teeth and tissue.

However, it is often difficult for a user of a dental instrument, whether an individual in his or her own mouth, or a dentist in a patient's mouth, to both utilize the particular instrument within the oral cavity and see what he or she is doing with the instrument. Specifically, it is often difficult to open one's mouth wide enough for an individual or dental practitioner to place the instrument or instruments therein and to see. In many cases, work done on teeth or tissue within an oral cavity must be viewed at awkward angles depending on where the work is being performed, and it is often difficult to allow sufficient light to shine within the oral cavity.

One solution involves utilizing directed light and/or mirrors to direct the light and allow a user to view teeth or tissue that may otherwise be difficult to view. Specifically, a dental mirror or mouth mirror is a relatively small mirror surface attached to an instrument, typically at an angle so that both light can be directed into an oral cavity and an individual or dental practitioner may see therein. Moreover, focused light sources, such as via strategically placed lamps or the like may be utilized to shine light into an oral cavity for more easily viewing teeth and tissue therein.

Other solutions may include dental props or retractors that may help to widen the oral cavity and prevent certain oral cavity features from blocking views, such as tongues, lips, cheeks or the like. These props or retractors may be utilized alone or together with light sources and mouth mirrors to gain better views within oral cavities.

Another solution involves utilizing cameras to see within oral cavities and aid an individual or a dental practitioner. An intraoral wand camera, for example, may be utilized to view within an oral cavity. Cameras have the advantage of providing clearer images, and may be magnified to show important features within an oral cavity. Thus, the intraoral cameras may be utilized not only to aid a dental practitioner in viewing the internal oral cavity, but to also show another individual, such as the patient, features the dental practitioner wishes to show the patient.

However, typical intraoral cameras are often separate from instruments that may be utilized to clean and/or treat teeth and tissue within an oral cavity. Thus, a user must manipulate both the camera and the instrument. It is often difficult for a user to align the camera as needed to view the region of the oral cavity that is being worked on by the instrument.

In some cases, cameras may be utilized in conjunction with instruments. For example, in U.S. Pat. No. 5,051,823 mounts a camera to an instrument at the location of the instrument's tool to help a dental practitioner view the region of the oral cavity worked on by the instrument. However, this involves the placement of a relatively bulky camera lens and housing precisely at the position on the instrument that must be slender and able to fit within tight locations within the oral cavity. Thus, the usage of the camera is limited, and the usage of the tool attached thereto is also limited.

Moreover, placement of the camera at the location of the tool does not provide an effective perspective for an individual or a dental practitioner to both utilize and view the oral cavity with the camera at the same time. Specifically, when utilizing the tool, the camera is necessarily placed in close proximity to the region of the oral cavity worked on by the tool. Indeed, the perspective is much too close to be able to adequately view the work being performed by the tool. In practice, one must utilize the tool without the benefit of the view from the camera, and then lift the tool away from the region worked on to view the results thereof.

A need, therefore, exists for a dental instrument camera apparatus that allows easy viewing of an oral cavity. Specifically, a need exists for a dental instrument camera apparatus that provides an individual a view of his or her oral cavity and/or for use by dental practitioners.

Moreover, a need exists for a dental instrument camera apparatus that may be utilized in conjunction with a tool on the dental instrument. More specifically, a need exists for a dental instrument camera apparatus that may be utilized at the same time as the dental tool to provide effective perspective by the user thereof at the time of using the tool.

In addition, a need exists for a dental instrument camera apparatus that may be combined with a light source for illumination of an oral cavity when viewed via the camera apparatus and the tool on the dental instrument. A need further exists for a dental instrument camera apparatus that allows simultaneous use of each of the light source, the camera and the tool.

Further, a need exists for a dental instrument camera apparatus that may be further utilized with known techniques for viewing within oral cavities, such as via utilizing external light sources and/or mirrored surfaces for directing light and/or directing views in hard to see regions of the oral cavity. Still further a need exists for a dental instrument camera apparatus that may allow a user, such as an individual or a dental practitioner, to view video wirelessly on a viewing device, such as a computer, tablet, smart phone, or other like viewing device.

SUMMARY OF THE INVENTION

The present invention relates to dental instruments having video capabilities. Specifically, the present invention relates to a dental instrument having a video camera for viewing a user's or patient's mouth when utilizing the dental instrument. More specifically, the dental instrument provides video output to a wireless device, such as a smart phone, tablet computer or other like computer. Methods of using the same are further provided.

To this end, in an embodiment of the present invention, a dental tool apparatus is provided. The dental tool apparatus comprises: a housing and a first end and a second end, wherein on the first end of the housing is a lens for a camera and a dental instrument extending from the first end of the housing, the dental instrument having a working tip, wherein the camera has a line of sight in line with the working tip of the dental instrument.

In an embodiment, the dental tool apparatus comprises an aperture in the first end of the housing, wherein the dental instrument extends from the aperture.

In an embodiment, dental instrument is removably attachable to the housing within the aperture.

In an embodiment, the dental tool apparatus further comprises: at least one light source on the first end of the housing for illuminating the working tip of the dental instrument.

In an embodiment, the at least one light source is a light emitting diode.

In an embodiment, the dental tool apparatus further comprises a motor within the housing for moving the dental instrument.

In an embodiment, the motor is coupled to a power source.

In an embodiment, the power source is rechargeable.

In an embodiment, the dental tool apparatus further comprises: a controller associated with the dental tool apparatus for controlling the dental tool apparatus.

In an embodiment, the dental instrument is selected from the group consisting of a powered dental brush, a gum stimulator, a mirror, a pick and a scaler.

In an alternate embodiment of the present invention, a dental tool system is provided. The dental tool system comprises: a dental tool apparatus comprising a housing, a first end and a second end, wherein on the first end of the housing is a lens for a camera and a dental instrument extending from the first end of the housing, the dental instrument having a working tip, wherein the camera has a line of sight in line with the working tip of the dental instrument; and a display associated with the dental tool apparatus for displaying images from the lens on the first end of the housing.

In an embodiment, the dental tool system further comprises: a base, wherein the dental tool apparatus is removably attachable to the base.

In an embodiment, the base comprises a recharging element, and further wherein the dental tool apparatus is electrically recharged when attached to the base.

In an embodiment, the display is wirelessly connected to the dental tool apparatus.

In an embodiment, the dental tool system further comprises: a plurality of holders within the base, wherein the base holds a plurality of dental instrument inserts within the holders.

In an embodiment, the display is a smart phone or a tablet computer.

In an embodiment, the dental tool apparatus further comprises a processing board.

In an embodiment, the processing board comprises a controller for controlling the dental tool apparatus.

In an embodiment, the processing board processes video that is received by the dental tool apparatus via the lens.

In an embodiment, the processing board wirelessly sends video to the display.

It is, therefore, an advantage and objective of the present invention to provide a dental instrument camera apparatus that allows easy viewing of an oral cavity.

Specifically, it is an advantage and objective of the present invention to provide a dental instrument camera apparatus that provides an individual a view of his or her oral cavity and/or for use by dental practitioners.

Moreover, it is an advantage and objective of the present invention to provide a dental instrument camera apparatus that may be utilized in conjunction with a tool on the dental instrument.

More specifically, it is an advantage and objective of the present invention to provide a dental instrument camera apparatus that may be utilized at the same time as the dental tool to provide effective perspective by the user thereof at the time of using the tool.

In addition, it is an advantage and objective of the present invention to provide a dental instrument camera apparatus that may be combined with a light source for illumination of an oral cavity when viewed via the camera apparatus and the tool on the dental instrument.

It is a further advantage and objective of the present invention to provide a dental instrument camera apparatus that allows simultaneous use of each of the light source, the camera and the tool.

Further, it is an advantage and objective of the present invention to provide a dental instrument camera apparatus that may be further utilized with known techniques for viewing within oral cavities, such as via utilizing external light sources and/or mirrored surfaces for directing light and/or directing views in hard to see regions of the oral cavity.

Still further, it is an advantage and objective of the present invention to provide a dental instrument camera apparatus that may allow a user, such as an individual or a dental practitioner, to view video wirelessly on a viewing device, such as a computer, tablet, smart phone, or other like viewing device.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 9 illustrates a perspective view of a dental instrument in an embodiment of the present invention.

FIG. 10 illustrates a cut-away side view of a dental instrument in an embodiment of the present invention.

FIGS. 11A-11C illustrate attachments for a dental instrument in an embodiment of the present invention.

DETAILED DESCRIPTION OF THE PRESENTLY PREFERRED EMBODIMENTS

The present invention relates to dental instruments having video capabilities. Specifically, the present invention relates to a dental instrument having a video camera for viewing a user's or patient's mouth when utilizing the dental instrument. More specifically, the dental instrument provides video output to a wireless device, such as a smart phone, tablet computer or other like computer. Methods of using the same are further provided.

Figure 1:
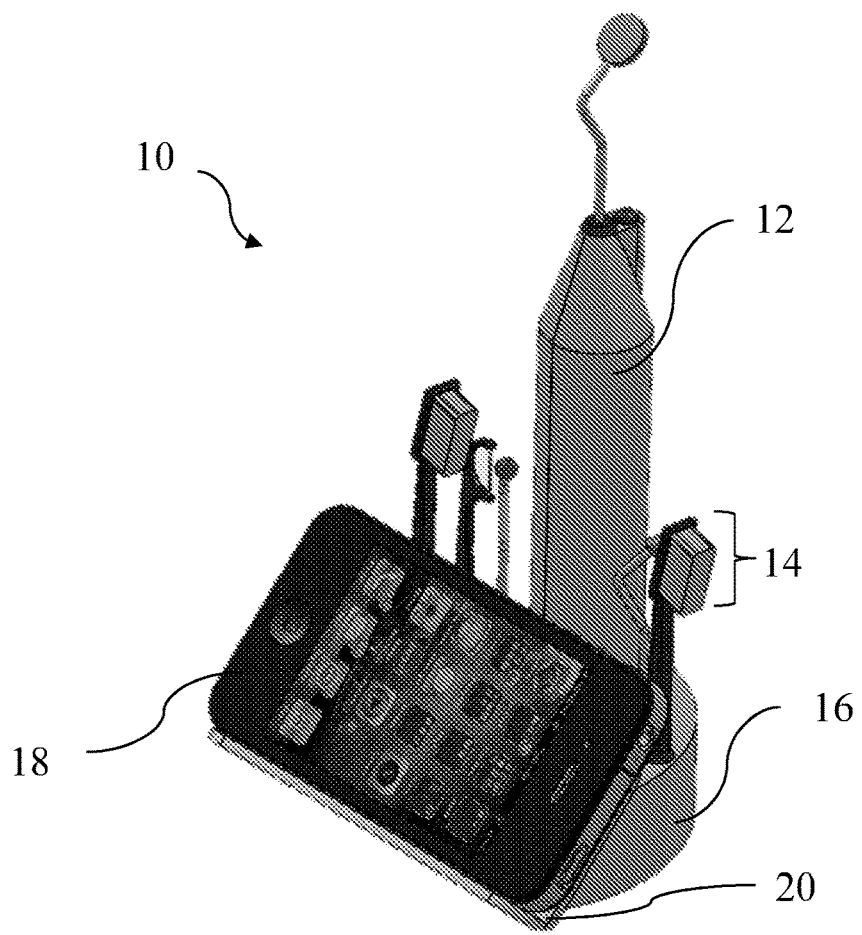
FIG. 1 illustrates a perspective view of a dental tool system for recording and/or viewing video and/or still photographs from a dental tool in an embodiment of the present invention.

Now referring to the figures, wherein like numerals refer to like parts, FIG. 1 illustrates a system 10 of the present invention, comprising, generally, a dental tool 12, a plurality of dental tool instrument tool inserts 14, a base 16, and a display device 18 for displaying video thereon. The dental tool 12 is illustrated and described in more detail below with reference to FIGS. 2-4.

The base 16 may hold the dental tool 12, the plurality of tool inserts 14, and may further hold the display device 18. Specifically, the base 16 may operate as a charging cradle for holding and/or charging the dental tool instrument 12 and/or the display device 18. More specifically, the base 16 may comprise a plurality of apertures or cradles for holding the dental tool 12 and the plurality of dental tool inserts 14.

The display device 18 may rest on or within a platform 20. The platform 20 may be angled so as to allow the display device 18 to be viewable by a user of the dental tool instrument 12 and/or a patient. The platform 20 may be adjustable so as to tilt or otherwise reposition the display device 18 for better view thereon, and may have a frame, flanges or other like holders for holding the display device 18 thereon or therein.

The display device 18 may preferably be a smart phone, such as an iPhone®, an Android® phone, a tablet computer, such as an iPad®, or other like display device that allows streaming video to be wirelessly sent from the dental tool 12, as described in more detail below. The display device 18 may preferably receive the wireless streaming video from the dental tool 12 via any manner apparent to one of ordinary skill in the art, such as via WiFi, 3G cellular telephone networks, Bluetooth®, or other like data transmission protocol, and via any video codec, such as MPEG4, M-JPEG or other like video codec.

The plurality of dental tool inserts 14 may be any dental tool instruments that may be useful for a dental practitioner to clean, repair, or otherwise tend to a patient's oral cavity. Common dental tool instruments may include brushes, scalers, mirrors, probes, syringes, drills, burs, excavators, burnishers, excavators, elevators, forceps, curettes, and any other like instrument that may be usefully employed from the dental tool instrument 12. In addition, it should be noted that the present invention may allow a plurality of instruments to be utilized at the same time, such as, for example, a dental mirror and a scaler to aid in the use of the scaler, as described in more detail below with respect to FIG. 4.

Figure 2:
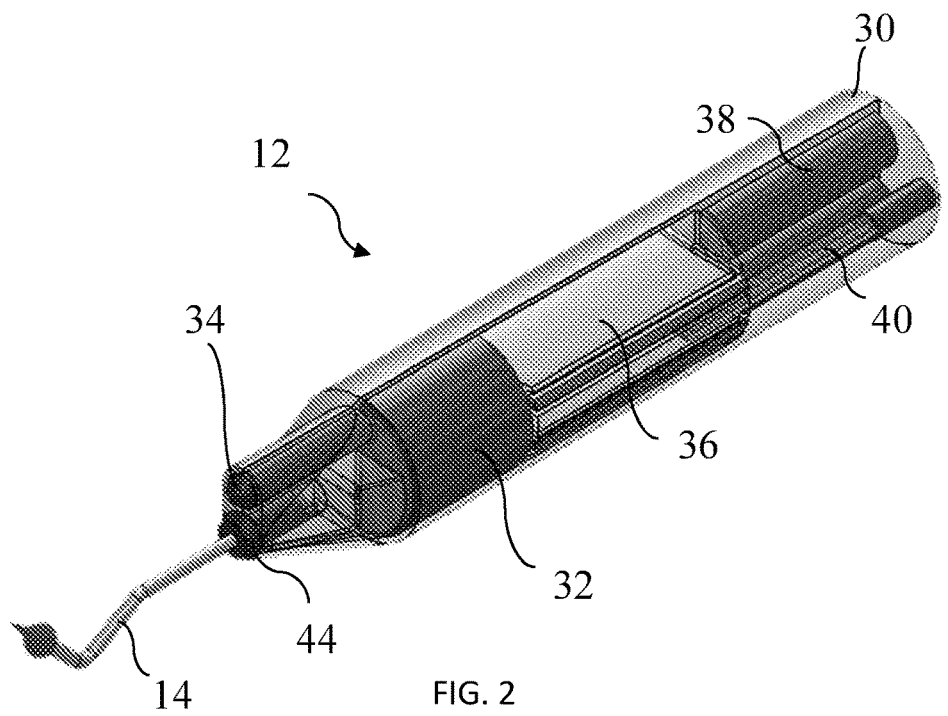
FIG. 2 illustrates a perspective view of a dental tool having a camera therein in an embodiment of the present invention.

FIG. 2 illustrates a cut-away perspective view of the dental tool 12 in an embodiment of the present invention. The dental tool 12 may generally comprise a housing 30 in which may be contained a camera 32 having a lens 34 for shooting video and/or still photographs, one or more processing boards 36, a rechargeable battery 38, a power cable 40, a charging input means 42, and a dental instrument insert aperture 44 for holding one or a plurality of dental instrument inserts 14. One or more light sources (not shown) may further be provided for directing illumination at the dental instrument insert 14 and/or the patient's oral cavity. The housing may be sealed and made of a material resistant to a moist environment, such as a metal or plastic, as apparent to one of ordinary skill in the art.

Figure 3:
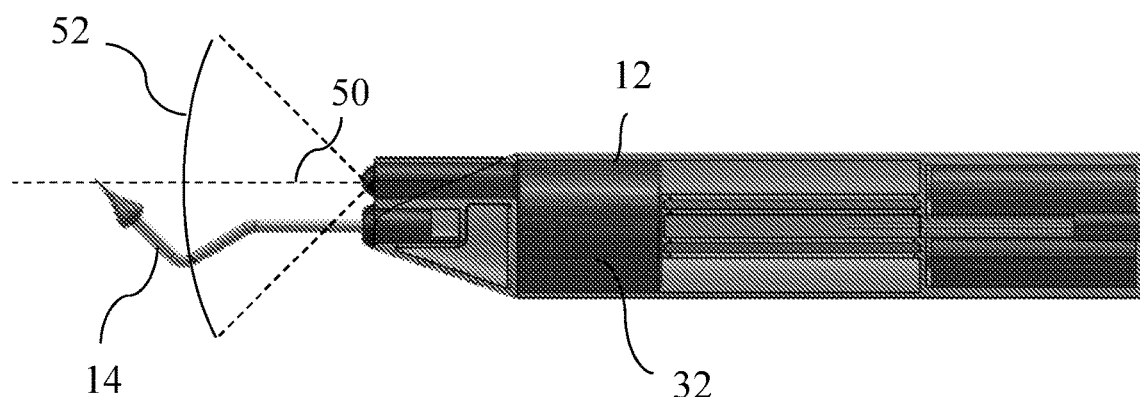
FIG. 3 illustrates a side view of a dental tool having a camera therein in an embodiment of the present invention.

In use, a user, such as a dental practitioner, may insert a dental instrument insert 14 into the dental instrument aperture 44, which may securely hold the dental instrument therein, such as via clamping means, frictional resistance means or the like. As illustrated in FIG. 3, the camera lens 34 is positioned on an end of the housing 30 and directed toward the tip of the dental instrument insert 14, providing a relatively wide viewing cone 52 for seeing the patient's oral cavity and the dental tool used within the patient's oral cavity. Specifically, the lens 34 may be adjacent the shaft of the dental instrument insert 14 and may provide a line-of-sight 50 for the camera that is roughly parallel with the shaft of the dental instrument insert 14. Thus, the dental instrument insert 14 and, specifically, the working tip of the dental instrument insert 14, may be easily viewable by the user of the dental tool 12 and/or the patient via the camera 32. In a preferred embodiment, the lens 34 may be aimed directly at the working tip of the dental instrument insert 14 for specific and precise viewing of the working tip of the dental instrument insert 14. One or more light sources (not shown), such as LEDs or the like, may further be used to illuminate the dental instrument insert 14 and/or the patient's oral cavity.

In a preferred embodiment, a dental mirror may be utilized to allow the camera 32 to record video and/or still photographs of an area that is ninety degrees, or any other angle, to the line-of-sight 50 of the camera 32, such as within a patient's oral cavity. Moreover, an illumination source emanating from the dental tool 12 may further be reflected off the dental mirror to aid in illuminating a patient's oral cavity.

Figure 4:
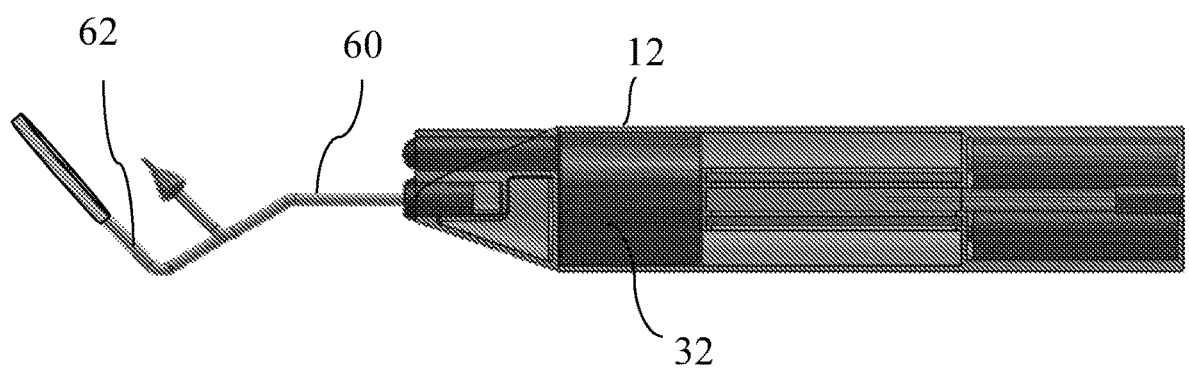
FIG. 4 illustrates a side view of a dental tool having a camera and a plurality of dental tool instrument inserts in an embodiment of the present invention.

As illustrated in FIG. 4, the dental tool 12 may include at least two dental instruments 60, 62, that may work together to allow a user thereof to more effectively utilize the dental tool 12 to clean and/or repair a patient's oral cavity. For example, and as illustrated in FIG. 4, the dental tool 12 may comprise the first dental instrument 60, which may be utilized to clean and/or repair teeth and/or tissue within a patient's oral cavity. Moreover, the dental tool 12 may further comprise the second dental instrument 62, such as a dental mirror, for allowing the user to see better the use of the dental instrument 12 within the patient's oral cavity. Of course, any dental instruments may be utilized together, as illustrated in FIG. 4, and the present invention should not be limited as described herein.

The camera 32 may thus be utilized to record and/or view within a patient's oral cavity where it may otherwise be difficult for the user and/or a patient to see. The dental tool 12 may use the dental instrument insert 14 thereon for working on teeth and/or tissue and the camera 32 may provide real-time video as the insert 14 is being used, streaming the video to the display device 18 or another display device that may accept the video stream wirelessly sent from the dental tool 12. Alternatively, the dental tool 12 may record video therein and/or process the video for streaming to a storage device, such as a smart phone or computer memory. Although the present invention shows a single display device 18, any number of display devices may be wirelessly connected to the dental tool 12 and may receive the video therefrom.

Figure 5:
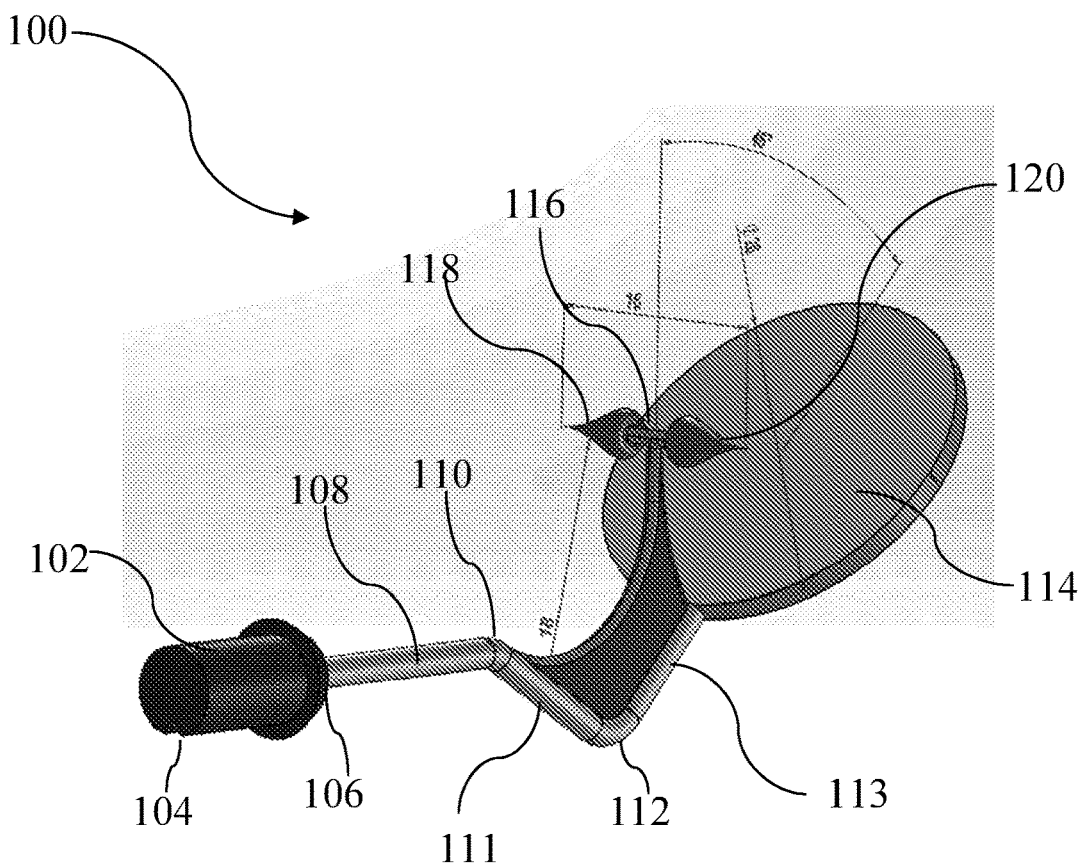
FIG. 5 illustrates a perspective view of an attachment for a dental tool in an embodiment of the present invention.

FIG. 5 illustrates an attachment 100 that may be utilized on a dental tool 12 as disclosed herein, and may be utilized as a swappable attachment that may be attached to and/or removed from the dental tool 12. Specifically, the attachment 100 may comprise a base 102 that may align with a mating receptacle on the dental tool 12 so that the base 102 may be inserted into the mating receptacle. A slot 104 may be disposed in the base 102 for aligning with a flange or nub in the receptacle to ensure that the attachment 100 is aligned properly. The base may further have a collar 106 at an end of the base 102 to prevent the base 102 from being inserted too far into the mating receptacle.

A stem 108 may extend from the base, and may have an angle 110 where the stem may be bent roughly about 45 degrees thereby forming a first stem section 111, and may further have a second bend 112 where the stem may be bent roughly 90 degrees thereby forming a second stem section 113. At a terminal end of the stem 108 may be a mirror 114 that may be angled at roughly 45 degrees relative to the base 106, based on the various bends in the stem 108, to allow the camera having a view roughly parallel with the base 106, to view inside a person's mouth when the attachment 100 is used on the dental tool 12. Extending from the step 108 may be a dental instrument 116, which may be, for example, a double-sided pick for engaging with a person's mouth, teeth, gums, or other like features. The double-sided pick may be utilized to engage a person's mouth in one direction by using one of the picks 118 and the double-sided pick may be utilized to engage a person's mouth in another direction by using the other pick 120.

Figure 6:
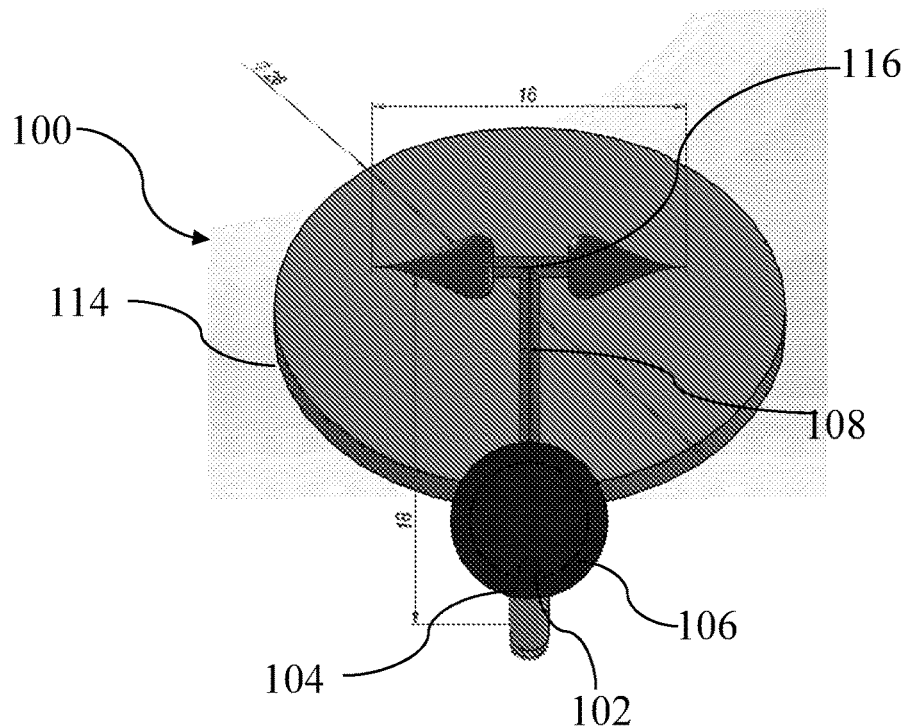
FIG. 6 illustrates a side view of an attachment for a dental tool in an embodiment of the present invention.
Figure 7:
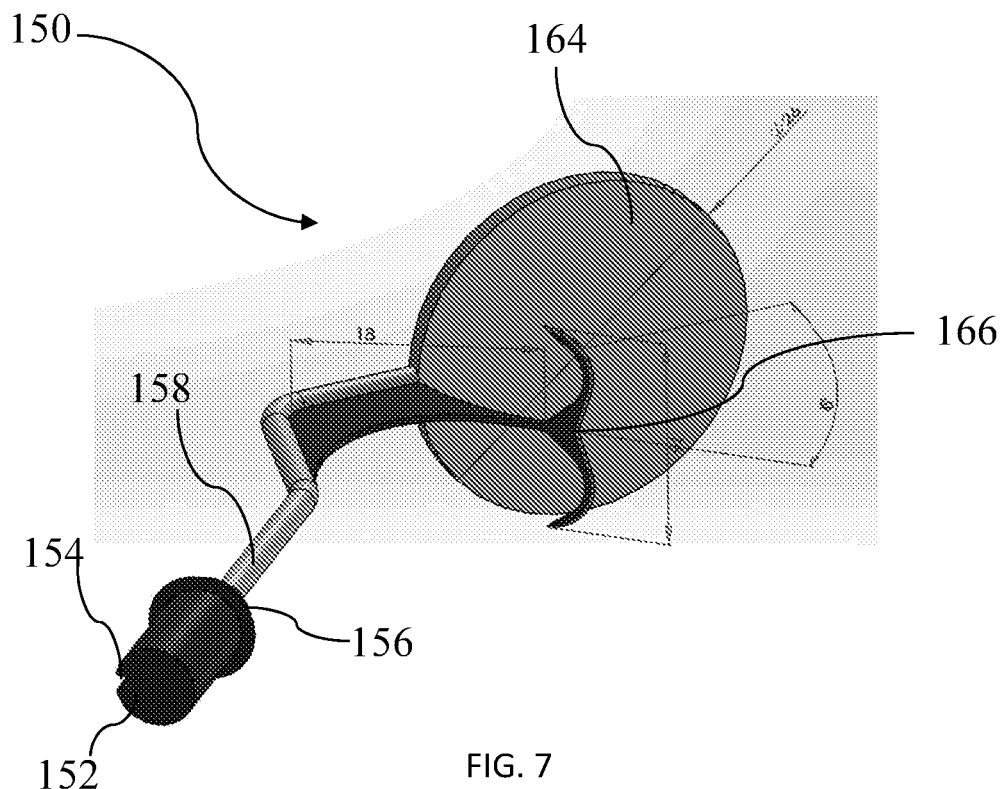
FIG. 7 illustrates a perspective view of an attachment for a dental tool in an alternate embodiment of the present invention.

FIG. 6 illustrates the attachment 100 in an end-view, showing the base 102, slot 104 and collar 106, and further showing the double-sided pick dental instrument 116 that may be utilized to engage a person's mouth, and the mirror 114 that may be utilized to allow the camera view inside the person's mouth when utilized.

In another embodiment of the present invention, an attachment 150 has a base 152 with a slot 154 and collar 156 for engaging a mating receptacle on the dental tool 12. Further, the attachment may have a stem 158 extending from the base 152 having a mirror 164 thereon, as described above. A double-sided dental instrument 166 may be utilized, such as a double-sided scalar to engage a user's mouth.

Figure 8:
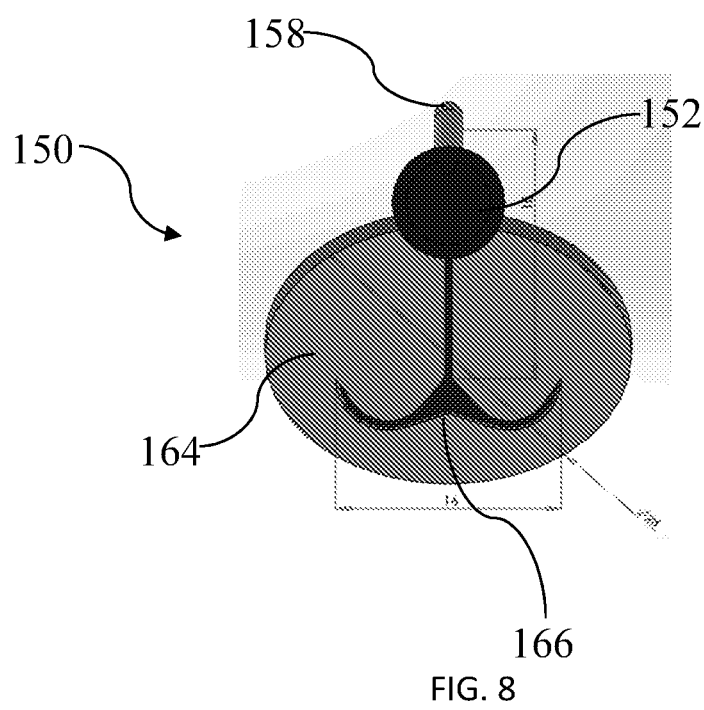
FIG. 8 illustrates a side view of an attachment for a dental tool in an alternate embodiment of the present invention.

Because the slot 154 is disposed on an opposite side of the base 152, as compared to base 102, described above, the mirror 164 and the dental instrument 166 may be disposed in an opposite direction than the dental instrument 116 and mirror 114, describe above, which may allow the dental instrument 166 to be utilized in a different manner than the dental instrument 116, described above. FIG. 8 shows the attachment 150 as it would be positioned when attached to the dental tool 12.

Referring now to FIG. 9, a perspective view of a dental instrument 200 is illustrated. The dental instrument 200 may comprise a body 202 and a dental instrument insert 204 extending from an end of the body 202 for use on a patient's oral cavity. Disposed adjacent the dental instrument insert 204 may be a camera lens 206. The camera lens 206 may allow an image or a video to be recorded, and may preferably have a line of sight that is roughly parallel with the dental instrument insert 204 extending from the body 202 of the dental instrument 200 and may be aimed at the working tip of the dental instrument insert 204. However, the camera lens 206 may further have a relatively wide angle to record or show a relatively large viewing field. Thus, the dental instrument 200 may display images and/or video of the working tip of the dental instrument insert 204 and, especially, during use of the same in a patient's oral cavity. In a preferred embodiment, the dental instrument 200 may have a plurality of lights 208, such as, for example, LEDs that may be ring the lens 206 and provide a sufficient light source for the recording and/or viewing of images and/or video. In another embodiment, the lights may be ultraviolet lights or a combination of visible and ultraviolet lights that may aid a user of the dental instrument 200 in viewing plaque on a patient's tooth, or for curing epoxies and the like within a patient's oral cavity.

FIG. 10 illustrates a cut-away side view of the dental instrument 200, in accordance with the present invention. Specifically, the dental instrument 200 may comprise the afore-mentioned dental instrument insert 204 that may preferably be removable from the body 202 so as to be replaceable with other dental instrument inserts, as shown below with respect to FIGS. 11A-11C. The dental instrument inset 204 may be placed within an aperture in the body 202, and when disposed therein may be mechanically tied to a motor and transmission 210, which may be electrically tied to a battery/power source 212 within the body 202. The dental instrument 200 may be powered via the battery/power source 212, and may preferably be rechargeable via charging element 214, which may be electrically coupled with a power source for charging the battery/power source 212, as needed.

The lens 206 and lights 208 may be disposed on end of the body on the same end as the dental instrument insert 204, such that the camera lens and lights may facilitate the recording and/or viewing of the dental instrument insert 204 when in use within a patient's oral cavity. Coupled to the lens 206 and lights 208 may be a main PCB board 216 that may control the recording and viewing of the images and/or video through the lens 206, and may further control the lights 208. The main PCB board 216 may allow a user to turn on or off the lens 206 for the recording and/or viewing of the same, or may allow a user to turn on or off the lights 208, as needed.

Thus, when in use, a user may insert a dental instrument insert 204 into the aperture of the body 202 of the dental instrument 200. The dental instrument 200 may have previously been coupled to a display device (not shown), either wired or, preferably, wirelessly, for viewing and/or recording images and/or video via lens 206. The user may have the ability to control the turning on or off of the lens 206 and/or the lights 208 via the display device (not shown), via the body 202, or via any other means or mechanism to control the same.

FIGS. 11A-11C illustrate various examples of dental instrument inserts 204 that may be utilized in the present invention. As illustrated in FIGS. 9-10, a powered dental brush may be the dental instrument insert 204. Alternatively, the dental instrument may be a gum stimulator 250 (as illustrated in FIG. 11A), a mirror 260 (as illustrated in FIG. 11B), a pick/scaler 270. Of course any instrument insert may be used, and the present invention should not be limited herein.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

I claim:

1. A dental tool system comprising:
   a dental tool body comprising:
   a housing having a distal end, a proximal end, and a handle;
   wherein the distal end of the housing defines an instrument aperture configured to receive a dental instrument;
   wherein the housing defines an axis that extends through the distal end, the proximal end, and the handle;
   a camera comprising a lens, wherein the lens is disposed on the distal end of the housing so as to provide a line of sight for the camera; and
   a plurality of functionally different dental instruments, collectively configured to be interchangeably inserted into the instrument aperture, and each configured to be removably inserted into the instrument aperture so as to be operatively coupled with the dental tool body, wherein each of the plurality of dental instruments comprises:
   a shaft having a proximal end and a distal end, wherein the proximal end is configured to be coupled with the instrument aperture, the shaft comprising an angled portion and a linear portion that is substantially parallel with the axis when the dental instrument is inserted into the instrument aperture; and
   a working tip disposed at the distal end of the shaft, wherein the working tip is within the line of sight of the camera when the dental instrument is inserted into the instrument aperture;
   wherein the angled portion of each of the dental instruments comprises substantially the same angle with respect to a line that is parallel to the axis as the angled portions of each other dental instrument of the plurality of dental instruments;
   wherein at least one of the plurality of dental instruments is an electrically-powered dental brush; and
   wherein the line of sight has a portion that is both generally parallel with the axis and in line with the working tip of one of the dental instruments that is inserted into the instrument aperture.

2. The dental tool system of claim 1, wherein at least one of the plurality of dental instruments is a gum stimulator, a mirror, a pick, or a scaler.

3. The dental tool system of claim 1, wherein the working tip of the powered dental brush is angled approximately 45 degrees from the axis.

4. The dental tool system of claim 1, wherein the line of sight of the camera is distally-oriented.

5. The dental tool system of claim 4, wherein the lens is disposed on the distal-most portion of the housing.

6. The dental tool system of claim 1, wherein the lens is disposed on the distal-most portion of the housing and wherein the instrument aperture is defined in the distal-most portion of the housing.

7. The dental tool system of claim 1, wherein the line of sight of the camera is fixed relative to the housing.

8. The dental tool system of claim 1, wherein the dental tool body further comprises a charging element disposed at the proximal end of the housing and configured for coupling with an electrical power source.

9. The dental tool system of claim 1, wherein each of the plurality of dental instruments further comprises a base disposed at the proximal end of the shaft, wherein the base is insertable into the instrument aperture.

10. The dental tool system of claim 1, wherein the dental tool body further comprises:
    a motor;
    wherein at least one of the plurality of dental instruments is configured to be removably inserted into the instrument aperture so as to be operatively coupled with the motor.

11. The dental tool system of claim 1, wherein the dental tool body further comprises:
    a light source disposed at the distal end of the housing and configured to illuminate the working tip of one of the plurality of dental instruments that is inserted into the instrument aperture.

12. The dental tool system of claim 1, wherein the dental tool body further comprises:
    a controller, disposed within the housing, configured to wirelessly transmit images captured by the camera to a user electronic device.

* * * * *